United States Patent [19]

Nagano et al.

[11] Patent Number: 4,736,068
[45] Date of Patent: Apr. 5, 1988

[54] TETRAHYDROPHTHALIMIDES AND THEIR PRODUCTION AND USE AS HERBICIDES

[75] Inventors: Eiki Nagano, Nishinomiya; Shunichi Hashimoto, Toyonaka; Ryo Yoshida, Kawanishi; Hiroshi Matsumoto, Toyonaka; Katsuzo Kamoshita, Osaka, all of Japan

[73] Assignee: Sumitomo Chemical Company, Limited, Osaka, Japan

[21] Appl. No.: 903,830

[22] Filed: Sep. 3, 1986

Related U.S. Application Data

[60] Continuation of Ser. No. 652,625, Sep. 20, 1984, abandoned, which is a division of Ser. No. 360,999, Mar. 23, 1982, Pat. No. 4,484,941.

[30] Foreign Application Priority Data

| Sep. 1, 1981 | [JP] | Japan | 56-138044 |
| Nov. 9, 1981 | [JP] | Japan | 56-180046 |
| Nov. 9, 1981 | [JP] | Japan | 56-180047 |
| Nov. 10, 1981 | [JP] | Japan | 56-180547 |
| Nov. 12, 1981 | [JP] | Japan | 56-182024 |
| Nov. 12, 1981 | [JP] | Japan | 56-182025 |
| Feb. 2, 1982 | [JP] | Japan | 57-15899 |

[51] Int. Cl.$^4$ .................... C07C 79/00; C07C 87/00
[52] U.S. Cl. .................... 568/588; 564/442
[58] Field of Search ............... 568/588, 709; 564/442

[56] References Cited

U.S. PATENT DOCUMENTS

| 3,686,331 | 8/1972 | O'Brien et al. | 568/588 |
| 3,830,849 | 8/1974 | Martin et al. | 568/588 |
| 3,878,224 | 4/1975 | Matsui et al. | 548/513 |
| 3,984,435 | 10/1976 | Matsui et al. | 71/96 |
| 4,001,272 | 1/1977 | Goddard | 71/96 |
| 4,006,185 | 2/1977 | Tobin et al. | 564/442 |
| 4,032,326 | 6/1977 | Goddard | 71/96 |
| 4,292,070 | 9/1981 | Wakabayashi et al. | 71/96 |

FOREIGN PATENT DOCUMENTS

2046754 11/1980 United Kingdom ............ 71/96

OTHER PUBLICATIONS

Vol. 81, pp. 94-101, J. Am. Chem. Soc. (1959).

Primary Examiner—Werren B. Lone
Attorney, Agent, or Firm—Birch, Stewart, Kolasch & Birch

[57] ABSTRACT

A compound of the formula:

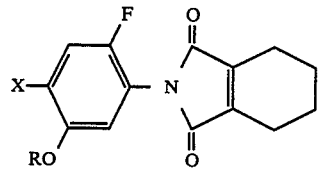

wherein X is a chlorine atom or a bromine atom and R is a $C_3$–$C_4$ alkenyl group or a $C_3$–$C_4$ alkynyl group, which is useful as a herbicide.

5 Claims, No Drawings

TETRAHYDROPHTHALIMIDES AND THEIR PRODUCTION AND USE AS HERBICIDES

This application is a continuation of application Ser. No. 652,625 filed on Sept. 20, 1984, now abandoned, which is a divisional of application Ser. No. 360,999 filed on Mar. 23, 1982 and now U.S. Pat. No. 4,484,941.

The present invention relates to N-(2-fluoro-4-halo-5-substituted phenyl)-3,4,5,6-tetrahydrophthalimide derivatives (hereinafter referred to as "tetrahydrophthalimide(s)"), and their production and use.

The tetrahydrophthalimides are representable by the formula:

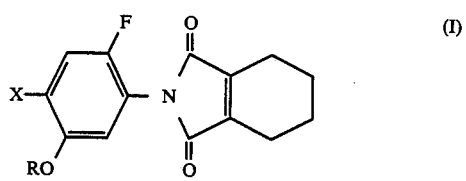

wherein X is a chlorine atom or a bromine atom and R is a C$_3$–C$_4$ alkenyl group (e.g. allyl) or a C$_3$–C$_4$ alkynyl group (e.g. 2-propynyl).

It is known that certain kinds of N-phenyltetrahydrophthalimides are effective as herbicides. For instance, the herbicidal use of 2-fluoro-4-chlorophenyltetrahydrophthalimide, 2,4-dichloro-5-isopropoxyphenyltetrahydrophthalimide, etc. is disclosed in U.S. Pat. No. 4,032,326, U.K. Patent Publication No. 2046754A, etc. However, their herbicidal effect is still not always satisfactory.

It has now been found that the tetrahydrophthalimides of formula (I) show a strong herbicidal activity against a wide variety of weeds including Gramineae weeds, Cyperaceae weeds and broad-leaved weeds at small doses and do not produce any material phytotoxicity on various agricultural crops. Examples of Gramineae weeds against which the tetrahydrophthalimides (I) show a herbicidal activity are barnyardgrass (*Echinochloa crus-galli*), green foxtail (*Setaria viridis*), large crabgrass (*Digitaria sanguinalis*), Johnsongrass (*Sorghum halepense*), wild oat (*Avena fatua*), water foxtail (*Alopecurus geniculatus*), goosegrass (*Eleusine indica*), annual bluegrass (*Poa annua*), bermudagrass (*Cynodon dactylon*), quackgrass (*Agropyron repens*), etc. Examples of Cyperaceae weeds are nutsedge sp. (*Cyperus* sp.), purple nutsedge (*Cyperus rotundus*), hardstem bulrush (*Scirpus juncoides*), nutsedge (*Cyperus serotinus*), water chestnut (*Eleocharis kuroguwai*), slender spikerush (*Eleocharis acicularis*), etc. Examples of broad-leaved weeds are tall morningglory (*Ipomoea purpurea*), velvetleaf (*Abutilon theophrasti*), sicklepod (*Cassia obtusifolia*), wild sunflower (*Helianthus annus*), cocklebur (*Xanthium pennsylvanicum*), wild mustard (*Brassica kaber*), common chickweed (*Stellaria media*), common purslane (*Portulaca oleracea*), jimsonweed (*Datura stramonium*), hemp sesbania (*Sesbania exaltata*), sun spurge (*Euphorbia helioscopia*), prickly sida (*Sida spinosa*), common ragweed (*Ambrosia artemisifolia*), smartweed sp. (*Polygonum* sp.), redroot pigweed (*Amaranthus retroflexus*), bedstraw (*Galium aparine*), pineappleweed (*Matricaria* spp.), birdseye speedwell (*Veronica persica*), wild buckwheat (*Polygonum convolvulus*), ladysthumb (*Polygonum persicaria*), beggarticks (Bidens spp.), common lambsquarters (*Chenopodium album*), black nightshade (*Solanum nigrum*), bindweed (*Calystegia japonica*), monochloria (*Monochoria vaginalis*), American waterwort (*Elatine americana*), false pimpernel (*Lindernia procumbens*), toothcup (*Rotala indica*), arrowhead (*Sagittaria pygmaea*), etc.

Accordingly, the tetrahydrophthalimides (I) can be used as herbicides applicable for field crops and vegetables as well as paddy rice. They are also useful as herbicides to be employed for orchard, lawn, pasture, tea garden, mulberry field, rubber plantation, forest, etc. applications.

The tetrahydrophthalimides (I) can be produced by various procedures, among which typical examples are shown below.

PROCEDURE A

The tetrahydrophthalimide (I) is obtainable by reacting an aniline of the formula:

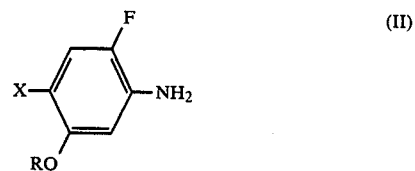

wherein X and R are each as defined above with 3,4,5,6-tetrahydrophthalic anhydride, in the absence or presence of an inert solvent (e.g. benzene, toluene, xylene, 1,4-dioxane, acetic acid, propionic acid) while heating. The reaction is normally accomplished at a temperature of 70° to 200° C. for a period of 0.5 to 5 hours. The molar ratio of the aniline (II) and the tetrahydrophthalic anhydride is preferred to be from 1:1.0 to 1:1.1.

PROCEDURE B

The tetrahydrophthalimide (I) is obtainable by reacting a hydroxyphenyltetrahydrophthalimide of the formula:

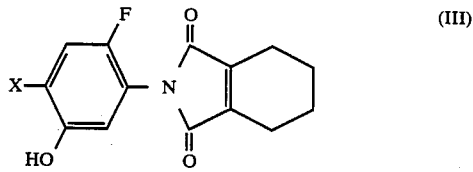

wherein X is as defined above with a halide of the formula: RY wherein Y is a chlorine atom, a bromine atom or an iodine atom and R is as defined above, usually in an inert solvent (e.g. dimethylformamide, dimethylsulfoxide) in the presence of a base such as an alkali metal carbonate (e.g. potassium carbonate), an alkali metal hydroxide (e.g. potassium hydroxide), an alkali metal hydride (e.g. sodium hydride) or an alkali metal alkoxide (e.g. sodium methoxide, sodium ethoxide). The most preferred base is an alkali metal carbonate. The reaction temperature is normally from 0° to 100° C., preferably from 40° to 90° C. The molar ratio of the hydroxyphenyltetrahydrophthalimide (III) and the halide is preferred to be from 1:1.0 to 1:1.1

The thus produced tetrahydrophthalimide (I) may be, when desired, purified by a per se conventional procedure such as recrystallization or column chromatography.

The aniline (II) as the starting material in Procedure A and the hydroxyphenyltetrahydrophthalimide (III) as the starting material in Procedure B can be produced from a phenol of the formula:

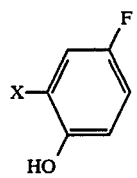

(IV)

wherein X is as defined above according to the following scheme:

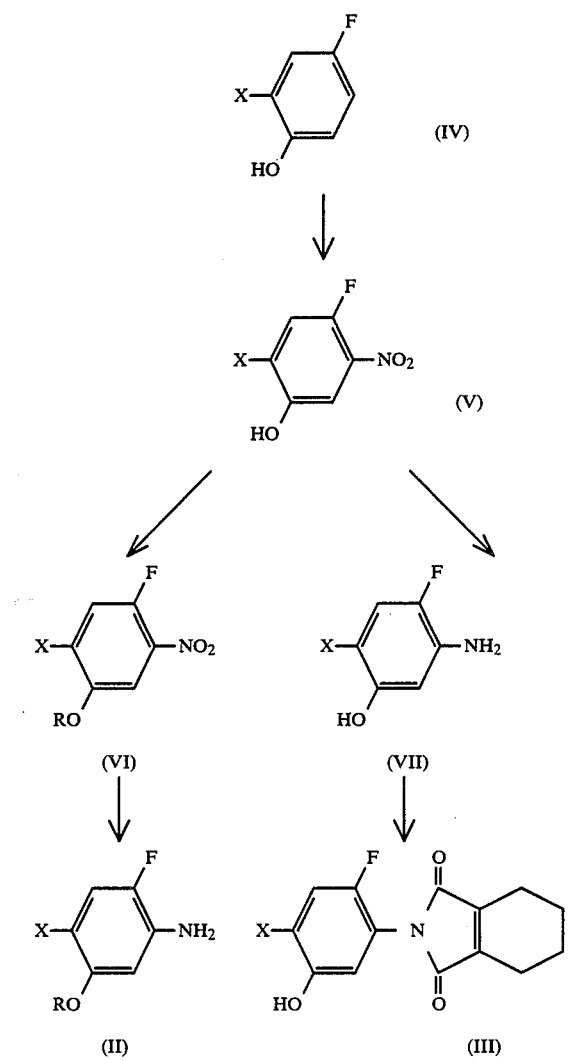

wherein X and R are each as defined above.

Specifically, the aniline (II) may be produced from the phenol (IV) by nitrating the same, subjecting the resultant nitrophenol (V) to alkenylation or alkynylation and reducing the resulting alkenyloxy- or alkynyloxy-nitrobenzene (VI). The hydroxyphenyltetrahydrophthalimide (III) can be manufactured from the phenol (IV) by nitrating the same, reducing the resultant nitrophenol (V) and reacting the resulting aminophenol (VII) with 3,4,5,6-tetrahydrophthalic anhydride.

Conversion of the phenol (IV) into the nitrophenol (V) may be accomplished by application of a per se conventional nitration procedure to the former. Usually, however, the indirect nitration which consists of the following three steps is favorable for achieving the selective nitration at the desired position:

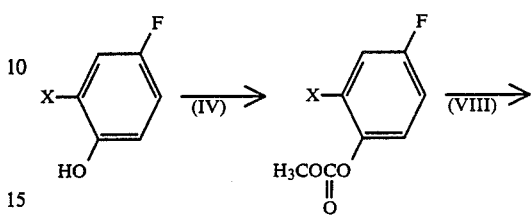

wherein X is as defined above. Thus, the phenol (IV) is converted into its alkali metal salt by treatment with an aqueous solution of an alkali metal hydroxide (e.g. sodium hydroxide, potassium hydroxide), and the resulting salt is reacted with an alkyl haloformate such as methyl chloroformate in water at a temperature of 0° to 10° C. The thus prepared carbonic ester (VIII) is nitrated with a mixture of conc. sulfuric acid and conc. nitric acid at room temperature. Then, the nitrobenzene (IX) thus obtained is hydrolyzed with an aqueous alkaline solution such as an aqueous sodium hydroxide solution at a temperature of 20° to 120° C. to give the nitrophenol (V).

The alkenylation or alkynylation for conversion of the nitrophenol (V) into the alkenyloxy- or alkynyloxynitrobenzene (VI) may be carried out by treatment of the former with an alkali metal carbonate (e.g. potassium carbonate), an alkali metal hydride (e.g. sodium hydride) or an alkali metal alkoxide (e.g. sodium methoxide) and reacting the resultant alkali metal salt with a halide of the formula: RY wherein R and Y are each as defined above in a polar solvent (e.g. water, dimethylformamide, acetonitrile, acetone, dimethylsulfoxide), usually at a temperature of 10° to 200° C., preferably of 30° to 100° C. The use of a phase transfer catalyst such as tetrabutylammonium bromide is favorable for smooth accomplishment of the reaction.

Reduction of the alkenyloxy- or alkynyloxy-nitrobenzene (VI) to the aniline (II) may be achieved by various procedures. For instance, there may be adopted reduction with iron powder. Namely, an acetic acid solution containing one molar amount of the compound (VI) is admixed with a 5% acetic acid solution containing 2 to 5 molar amount of iron powder such as reductive iron or electrolytic iron at a temperature of 80° to 100° C. and then the reaction is effected at a temperature of 80° to 120° C., preferably of 90° to 110° C., for a period of 0.5 to 5 hours.

Conversion of the nitrophenol (V) into the aminophenol (VII) may be accomplished by any per se conventional reduction procedure for changing a nitro group to an amino group. Examples of such reduction procedure are catalytic reduction, reduction with iron powder, reduction with sodium sulfide, reduction with sulfurated sodium borohydride, etc. For instance, treatment of one molar amount of the nitrophenol (V) with a 3 molar amount of hydrogen in the presence of a 1/10 to 1/100 molar amount of platinum dioxide in an inert solvent (e.g. ethanol, ethyl acetate) at room temperature under atmospheric pressure affords the aminophenol (VII). Further, for instance, treatment of one molar amount of the nitrophenol (V) with a 2 to 5 molar amount of iron powder such as reductive iron or electrolytic iron in a 5% acetic acid solution or a dilute hydrochloric acid solution at a temperature of 80° to 100° C. for a period of 1 to 5 hours produces the aminophenol (VII).

For production of the hydroxyphenyltetrahydrophthalimide (III) from the aminophenol (VII), the latter is reacted with 3,4,5,6-tetrahydrophthalic anhydride in an inert solvent (e.g. acetic acid) while refluxing for a period of 1 to 6 hours, preferably of 2 to 4 hours.

Still, the phenol (IV) is known (cf. Finger et al.: J.Am.Chem.Soc., 81, 94 (1959)).

Practical and presently preferred embodiments of the production of the objective tetrahydrophthalimide (I) as well as the intermediary compounds including those of the formulas:

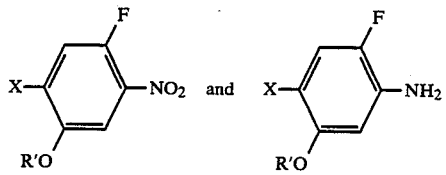

wherein R' is a hydrogen atom, a $C_3$–$C_4$ alkenyl group or a $C_3$–$C_4$ alkynyl group and X is as defined above are illustratively shown below:

EXAMPLE 1

Production of the tetrahydrophthalimide (I: X=Cl; R=CH≡CCH$_2$—):

To a solution of N-(4-chloro-2-fluoro-5-hydroxyphenyl)-3,4,5,6-tetrahydrophthalimide (1 g) in dimethylformamide (10 ml), there was added anhydrous potassium carbonate (0.34 g) while stirring at room temperature. After stirring for 30 minutes at about 40° C., propargyl bromide (1 g) was added thereto, and the resultant mixture was stirred for 3 hours at 50°–60° C. After being allowed to cool to room temperature, the mixture was poured into water and extracted with ether. The ether layer was washed with water, dried over anhydrous sodium sulfate and concentrated. The residue was purified by silica gel chromatography to obtain 0.8 g of N-[4-chloro-2-fluoro-5-(2-propynyloxy)phenyl]-3,4,5,6-tetrahydrophthalimide (Compound No. 3). M.P., 136.4° C.

Elementary analysis (%): Calcd.: C, 61.09; H, 4.00; N, 4.20; Found: C, 61.18; H, 4.19; N, 3.92.

NMR (CDCl$_3$) δ (ppm): 1.8 (4H, m), 2.4 (4H, m), 2.55 (1H), 4.7 (1H), 6.95 (1H, d, J=6 Hz), 7.25 (1H, d, J=10 Hz).

IR $\nu^{nujol}$ (cm$^{-1}$): 3260, 1700.

EXAMPLE 2

Production of the tetrahydrophthalimide (I: X=Cl; R=2-propynyl):

4-Chloro-2-fluoro-5-(2-propynyloxy)aniline (1.9 g) and 3,4,5,6-tetrahydrophthalic anhydride (1.52 g) were dissolved in acetic acid (20 ml) and refluxed for 3 hours. The resultant mixture was allowed to cool to room temperature and poured into water, followed by extraction with ether. The extract was washed with water, dried over anhydrous sodium sulfate and subjected to filtration. The filtrate was concentrated under reduced pressure and the residue was purified by silica gel chromatography to obtain 1.3 g of N-[4-chloro-2-fluoro-5-(2-propynyloxy)phenyl]-3,4,5,6-tetrahydrophthalimide (Compound No. 3). M.P. 136.4° C.

Examples of the tetrahydrohalimide (I) produced in the same manner as above are shown in Table 1.

TABLE 1

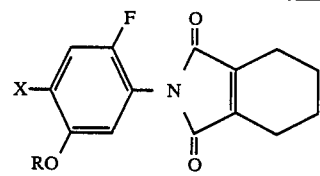

| Compound No. | X | R | Physical property |
|---|---|---|---|
| 1 | Cl | CH$_2$=CHCH$_2$— | M.P. 56–57° C. |
| 2 | Cl | CH$_2$=CHCH— $\|$ CH$_3$ | $n_D^{25.5}$ 1.5512 |
| 3 | Cl | CH≡CCH$_2$— | M.P. 136.4° C. |
| 4 | Cl | CH≡CCH— $\|$ CH$_3$ | M.P. 115–116° C. |
| 5 | Br | CH≡CCH$_2$— | M.P. 127–128° C. |
| 6 | Br | CH$_2$=CHCH$_2$— | M.P. 69–70° C. |

EXAMPLE 3

Production of the aniline (II: X=Cl; R=CH≡CCH$_2$—):

A suspension of electrolytic iron powder (3.5 g) in a 5% aqueous acetic acid solution was heated to 90° C., and a solution of 4-chloro-2-fluoro-5-(2-propynyloxy)-nitrobenzene (5.7 g) in acetic acid (40 ml) was dropwise added thereto at the same temperature. The resultant mixture was stirred at 90°–105° C. for 1 hour and allowed to cool to room temperature. Water (200 ml) was added thereto. Insoluble materials were filtered, and the filtrate was neutralized, followed by extraction with ethyl acetate. The extract was dried over anhydrous magnesium sulfate and concentrated. The residue was washed with petroleum ether and carbon tetrachloride to obtain 3.6 g of 4-chloro-2-fluoro-5-(2-propynyloxy)aniline. M.P. 61.0°–61.5° C.

NMR (CDCl$_3$) δ(ppm): 2.5 (1H, t, J=2 Hz), 3.4–4.2 (2H, m, J=16 Hz), 4.15 (2H, d, J=2 Hz), 6.5 (1H, d, J=8 Hz), 6.95 (1H, d, J=10 Hz).

IR $\nu_{max}$ (cm$^{-1}$): 3460, 3360, 3280, 2100.

Some examples of the anilines (II) produced in the same manner as above are shown in Table 2.

TABLE 2

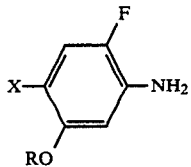

| X  | R                | Physical property              |
|----|------------------|--------------------------------|
| Cl | CH$_2$=CHCH$_2$— | n$_D^{19.0}$ 1.5598            |
| Cl | CH≡CCH$_2$—      | M.P. 61.0–61.5° C.             |
| Cl | CH≡CCH—<br>\|<br>CH$_3$ | M.P. 67.0–68.0° C.      |

EXAMPLE 4

Production of the hydroxyphenyltetrahydrophthalimide (III: X=Cl):

2-Chloro-4-fluoro-5-aminophenol (6.6 g) and 3,4,5,6-tetrahydrophthalic anhydride (6 g) were dissolved in acetic acid (20 ml) and refluxed for 2 hours. The resultant mixture was allowed to cool to room temperature and poured into ice-water, followed by extraction with ether. The ether extract was washed with a saturated sodium hydrogen carbonate solution and water in this order, dried over anhydrous magnesium sulfate and concentrated. The residue was purified by silica gel chromatography to obtain 4.0 g of N-(4-chloro-2-fluoro-5-hydroxyphenyl)-3,4,5,6-tetrahydrophthalimide. M.P., 151° C.

NMR (CDCl$_3$, D$_6$-DMSO) δ (ppm): 1.5–2.0 (4H, m), 2.1–2.6 (4H, m), 6.8 (1H, d, J=6 Hz), 7.15 (1H, d, J=10 Hz).

IR ν$_{max}^{nujol}$ (cm$^{-1}$): 3380, 1680.

Example 5

Production of the hydroxyphenyltetrahydrophthalimide (III: X=Br):

In the same manner as in Example 4 but using 2-bromo-4-fluoro-5-aminophenol in place of 2-chloro-4-fluoro-5-aminophenol, there was produced N-(4-bromo-2-fluoro-5-hydroxyphenyl)-3,4,5,6-tetrahydrophthalimide. M.P., 167°–168° C.

NMR (CDCl$_3$, D$_6$-DMSO) δ (ppm): 1.5–2.0 (4H, m), 2.1–2.7 (4H, m), 6.8 (1H, d, J=6 Hz), 7.25 (1H, d, J=10 Hz).

IR ν$_{max}^{nujol}$ (cm$^{-1}$): 3380, 1690.

EXAMPLE 6

Production of the alkynyloxy-nitrobenzene (VI: X=Cl; R=CH≡CCH$_2$—):

To a solution of 2-chloro-4-fluoro-5-nitrophenol (19.1 g) in acetonitrile (100 ml), there was added anhydrous potassium carbonate (8 g). After stirring at room temperature for several minutes, propargyl bromide (14 g) was added thereto, and the resultant mixture was heated under reflux for 3 hours. After being allowed to cool to room temperature, water was added thereto, and the reaction mixture was extracted with ether. The ether extract was washed with a 5% aqueous sodium hydroxide solution and water in this order, dried over anhydrous magnesium sulfate and subjected to filtration. The filtrate was concentrated under reduced pressure, and the residue was recrystallized from ethanol to obtain 13.5 g of 4-chloro-2-fluoro-5-(2-propynyloxy)nitrobenzene. M.P. 88°–89° C.

NMR (CDCl$_3$) δ (ppm): 2.55 (1H, t, J=3 Hz), 4.78 (2H, d, J=3 Hz), 7.35 (1H, d, J=10 Hz), 7.8 (1H, d, J=6 Hz).

Some of the alkenyloxy- or alkynyloxy-nitrobenzene (VI) compounds produced in the same manner as above are shown in Table 3.

TABLE 3

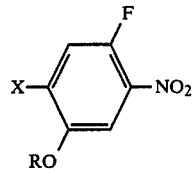

| X  | R                        | Physical property       |
|----|--------------------------|-------------------------|
| Cl | —CH$_2$CH=CH$_2$         | n$_D^{17.0}$ 1.5601     |
| Cl | —CHCH=CH$_2$<br>\|<br>CH$_3$ | M.P. 41.0–41.5° C.  |
| Cl | —CH$_2$C≡CH              | M.P. 88–89° C.          |
| Cl | —CHC≡CH<br>\|<br>CH$_3$  | M.P. 87–88° C.          |

EXAMPLE 7

Production of tthe aminophenol (VII: X=Cl):

A suspension of 2-chloro-4-fluoro-5-nitrophenol (9.17 g) and platinum dioxide (500 mg) in ethanol (120 ml) was subjected to catalytic reduction with hydrogen under room temperature and atmospheric pressure until a designed amount of hydrogen was absorbed. The catalyst was removed by filtration, and the filtrate was concentrated. The residue was extracted with ether, and the ether layer was concentrated to obtain 6.6 g of 3-amino-6-chloro-4-fluorophenol. M.P., 145°–146° C. (decomp.).

NMR (CDCl$_3$, D$_6$-DMSO) δ (ppm): 6.4 (1H, d, J=8 Hz), 6.85 (1H, d, J=11 Hz).

IR ν$_{max}^{nujol}$ (cm$^{-1}$): 3400, 3320.

EXAMPLE 8

Production of the aminophenol (VII: X=Br):

In the same manner as above but using 2-bromo-4-fluoro-5-nitrophenol in place of 2-chloro-4-fluoro-5-nitrophenol, there was produced 3-amino-6-bromo-4-fluorophenol. M.P., 129°–130.5° C. (decomp.).

NMR (CDCl$_3$, D$_6$-DMSO) δ (ppm): 6.57 (1H, d, J=8 Hz), 7.1 (1H, d, J=11 Hz).

IR ν$_{max}^{nujol}$ (cm$^{-1}$): 3400, 3320.

EXAMPLE 9

Production of the nitrophenol (V: X=Cl):

2-Chloro-4-fluorophenol (83.4 g) was added to a solution of sodium hydroxide (27.7 g) in water (450 ml), and methyl chloroformate (69.2 g) was dropwise added thereto at a temperature of below 10° C. Precipitated crystals were collected by filtration and washed with water to give methyl (2-chloro-4-fluorophenyl)formate (134.8 g). M.P., 69°–71° C.

Methyl (2-chloro-4-fluorophenyl)formate (134.8 g) obtained above was suspended in conc. sulfuric acid (50 ml). To the suspension, a mixture of conc. sulfuric acid (50 ml) and conc. nitric acid (50 ml) was added at about 30° C., and the mixture was stirred for 1 hour at this temperature. The reaction mixture was poured into ice water, and precipitated crystals were collected and washed with water. Methyl (2chloro-4-fluoro-5-nitrophenyl)formate (143 g) was thus obtained. M.P., 53°–55° C.

The product obtained as above was combined with sodium hydroxide (27 g) and water (300 ml), and the resultant mixture was refluxed for 4 hours. Precipitated insoluble materials were filtered using a celite, and the filtrate was acidified with conc. hydrochloric acid. Precipitated crystals were filtered and washed with water to obtain 76.3 g of 2-chloro-4-fluoro-5-nitrophenol. M.P. 106°–107° C.

NMR (CDCl$_3$, D$_6$-DMSO) δ (ppm): 7.25 (1H, d, J=10 Hz), 7.64 (1H, d, J=6 Hz).

IR $\nu_{max}^{nujol}$ (cm$^{-1}$): 3370.

EXAMPLE 10

Production of the nitrophenol (V: X=Br):

2-Bromo-4-fluorophenol (28 g) was added to a solution of sodium hydroxide (7 g) in water (100 ml), and methyl chloroformate was dropwise added thereto at a temperature of below 10° C. Precipitated crystals were collected by filtration and washed with water to give methyl (2-bromo-4-fluorophenyl)formate (41 g). M.P., 80.7° C.

The thus obtained methyl (2-bromo-4-fluorophenyl)formate was suspended in conc. sulfuric acid (13 ml). To the suspension, a mixture of conc. sulfuric acid (13 ml) and conc. nitric acid (13 ml) was added at about 30° C. The mixture was stirred for 30 minutes and poured onto ice. Precipitated crystals were thoroughly washed with water, whereby yellow crystals of methyl (2-bromo-4-fluoro-5-nitrophenyl)formate (38.3 g) were obtained. M.P., 63.5°–64.5° C.

The product thus obtained was refluxed together with sodium hydroxide (6.2 g) and water (100 ml) for 3 hours. Insoluble materials were filtered, and the filtrate was acidified with hydrochloric acid. Precipitated crystals were collected by filtration and washed with water to obtain 25 g of 2-bromo-4-fluoro-5-nitrophenol. M.P., 126°–127° C.

NMR (CDCl$_3$, D$_6$-DMSO) δ (ppm): 7.42 (1H, d, J=10 Hz), 7.65 (1H, d, J=6 Hz).

IR $\nu_{max}^{nujol}$ (cm$^{-1}$): 3450.

In the practical usage of the tetrahydrophthalimides (I), they may be applied as such or in any preparation form such as wettable powders, emulsifiable concentrates, granules, suspensions or dusts.

In producing such a preparation form, a solid or liquid carrier may be used. As for the solid carrier, there may be exemplified mineral powders (e.g. kaolin, bentonite, montmorillonite, talc, diatomaceous earth, mica, vermiculite, gypsum, calcium carbonate, apatite, synthetic water-containing silicon hydroxide), vegetable powders (e.g. soybean powder, wheat flour, wooden powder, tabacco powder, starch, crystalline cellulose), high molecular weight compounds (e.g. petroleum resin, polyvinyl chloride, dammar gum, ketone resin), alumina, wax and the like.

As for the liquid carrier, ther may be exemplified alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, poyoxyethylene fatty acid esters, sorbitan fatty acid esters polyoxyethylene sorbitan fatty acid esters, oxyethyleneoxypropylene polymers, polyoxyethylene alkylphosphates, fatty acid salts, alkyl sulfates, alkyl sulfonates, alkylaryl sulfonates, alkyl phosphates, polyoxyethylene alkyl sulfate, quaternary ammonium salts, and the like. But the surface active agent is not of course limited to these compounds. And, if necessary, gelatin, casein, sodium alginate, starch, agar, polyvinyl alcohol, ligninsulfonic acid or the like may be used as an auxiliary agent.

In tthe preparation of a herbicidal composition, the content of the tetrahydrophthalimide (I) may be from 1 to 95% by weight, preferably from 3 to 80% by weight.

The tetrahydrophthalimide (I) of the invention may be used together with other herbicides to improve their activity as herbicides, and in some cases, a synergistic effect can be expected. Further, they may be also applied in combination with insecticides, nematocides, fungicides, plant growth regulators or fertilizers, depending upon needs.

The dosage rate of the tetrahydrophthalimide (I) may vary depending on their kinds, the sorts of cultivated plants, the modes of application, etc. Generally, however, the doage rate is from 0.1 to 50 grams, preferably from 0.5 to 30 grams, of the active ingredient per are.

Practical embodiments of the herbicidal composition according to the invention are illustratively shown in the following examples wherein parts and % are by wight.

PREPARATION EXAMPLE 1

Eighty parts of Compound No. 1, 2 or 3, 3 parts of alkylsulfate, 2 parts of ligninsulfonate and 15 parts of water-containing silicon hydroxide are well mixed while being powdered to obtain a wettable powder.

PREPARATION EXAMPLE 2

Ten parts of Compound No. 1, 2 or 5, 3 parts of alkylarylsulfate, 7 parts of polyoxyethylene alkylaryl ether, 60 parts of cyclohexanone and 20 parts of xylene are well mixed while being powdered to obtain an emulsifiable concentrate.

PREPARATION EXAMPLE 3

Five parts of Compound No. 1 or 2, 1 part of water-containing silicon hydroxide, 35 parts of bentonite and 59 parts of kaolin are well mixed while being powdered. The mixture is then kneaded with water, granulated and dried to obtain a granule.

PREPARATION EXAMPLE 4

Three parts of Compound No. 1, 2 or 3, 0.3 part of isoprpyl phosphate, 66.7 parts of kaolin and 30 parts of talc are well mixed while being powdered to obtain a dust.

PREPARATION EXAMPLE 5

Twenty parts of Compound No. 6 is mixed with 60 parts of an aqueous solution containing 3% polyoxyethylene sorbitan monolaurate and grained until the particle size of the active ingredient becomes less than 3 microns. Twenty parts of an aqueous solution containing 3% of sodium alginate as a dispersing agent is introduced therein to obtain a suspension.

The application of the tetrahydrophthalimides (I) as herbicides will be illustratively shown in the following Examples wherein the phytotoxicity to cultivated plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and control weeds, respectively. The rating values in the paddy field test alone were calculated from the dry weight of the test plants.

| Rating value | Fresh weight (percentage to untreated plot) (%) | |
|---|---|---|
| | Crop plant | Weeds |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following control compounds were used in the Examples:

| Compound No. | Structure | Remarks |
|---|---|---|
| A | (4-chloro-2-fluorophenyl)-tetrahydrophthalimide | U.S. Pat. No. 4,032,326 |
| B | (2,4-dichloro-5-isopropoxyphenyl)-tetrahydrophthalimide | U.K. Patent Publn. No. 2046754A |
| C | $(CH_3)_2CHNH$— and —$HNCH_2CH_3$ substituted chloro-triazine | Atrazine |

TEST EXAMPLE 1

Plastic trays (35 cm×25 cm×10 cm) were filled with upland field soil, and the seeds of corn, velvetleaf, sunflower, sicklepod, tall morningglory, wild mustard and common chickweed were separately sowed in the trays and grown for 2 weeks in the greenhouse. Each of two trays was set in a frame (50 cm×100 cm×40 cm) and a designed amount of the test compound was sprayed to the foliage of the test plants over the top by means of a small hand sprayer. After the spraying, the test plants were further grown for 3 weeks in the greenhouse, and herbicidal activity and phytotoxicity were examined. The results are shown in Table 4. In this foliar treatment, the test compounds were formulated into an emulsifiable concentrate according to Preparation Example 2 and applied by dispersing it in 25 ml of water with the addition of a spreading agent. At the time of application, the test plants were in a 1 to 3-leaf stage and 2 to 20 cm in height.

TABLE 4

| Compound No. | Dosage (weight of active ingredient, g/are) | Phytotoxicity Corn | Herbicidal activity | | | | | |
|---|---|---|---|---|---|---|---|---|
| | | | Velvetleaf | Sunflower | Sicklepod | Tall morningglory | Wild mustard | Common chickweed |
| 3 | 1.25 | 1 | 5 | 5 | 5 | 5 | 5 | 5 |
| | 0.63 | 0 | 5 | 5 | 4 | 5 | 5 | 4 |
| | 0.32 | 0 | 5 | 5 | 4 | 5 | 3 | 3 |
| 5 | 1.25 | 1 | 5 | 5 | 5 | 5 | 5 | 5 |
| | 0.63 | 1 | 5 | 5 | 4 | 5 | 5 | 4 |
| | 0.32 | 0 | 5 | 4 | 3 | 5 | 5 | 3 |
| A | 10 | 3 | 5 | 5 | 4 | 5 | 5 | 2 |

TABLE 4-continued

| Compound No. | Dosage (weight of active ingredient, g/are) | Phytotoxicity Corn | Herbicidal activity | | | | | |
|---|---|---|---|---|---|---|---|---|
| | | | Velvetleaf | Sunflower | Sicklepod | Tall morningglory | Wild mustard | Common chickweed |
| | 5 | 3 | 5 | 5 | 4 | 5 | 4 | 1 |
| | 2.5 | 2 | 5 | 4 | 3 | 4 | 3 | 1 |
| | 1.25 | 1 | 3 | 2 | 1 | 3 | 2 | 0 |
| B | 10 | 3 | 5 | 5 | 4 | 5 | 5 | 3 |
| | 5 | 2 | 5 | 5 | 3 | 4 | 4 | 2 |
| | 2.5 | 2 | 4 | 4 | 2 | 4 | 3 | 1 |
| | 1.25 | 0 | 2 | 3 | 0 | 2 | 1 | 0 |
| C | 10 | 0 | 5 | 5 | 2 | 5 | 5 | 5 |
| | 5 | 0 | 3 | 5 | 0 | 4 | 5 | 5 |

TEST EXAMPLE 2

Plastic beakers (diameter, 10 cm; height, 10 cm) were filled with upland field soil, and the seeds of corn, barnyardgrass, wild oat, wild mustard and velvetleaf were separately sowed in the beakers and grown for 2 weeks in the greenhouse. A designed amount of the test compound was sprayed to the foliage of the test plants by means of a small hand sprayer. After the spraying, the test plants were futher grown for 3 weeks in the greenhouse, and herbicidal activity was examined. The results are shown in Table 5. In this foliar treatment, the test compounds were formulated into an emulsifiable concentrate according to Preparation Example 2 and applied at a spray volume of 5 liters per are by dispersing it in water with the addition of a spreading agent.

TABLE 5

| Compound No. | Dosage (weight of active ingredient, g/are) | Phytotoxicity Corn | Herbicidal activity | | | |
|---|---|---|---|---|---|---|
| | | | Barnyardgrass | Wild oat | Wild mustard | Velvetleaf |
| 1 | 5 | 1 | 5 | 5 | 5 | 5 |
| | 1.25 | 1 | 4 | 4 | 5 | 5 |
| 2 | 5 | 1 | 5 | 5 | 5 | 5 |
| | 1.25 | 0 | 5 | 4 | 5 | 5 |
| 3 | 5 | 1 | 5 | 5 | 5 | 5 |
| | 1.25 | 1 | 5 | 5 | 5 | 5 |
| 4 | 5 | 1 | 5 | 5 | 5 | 5 |
| | 1.25 | 1 | 5 | 5 | 5 | 5 |
| 5 | 5 | 1 | 5 | 5 | 5 | 5 |
| | 1.25 | 0 | 3 | 4 | 5 | 5 |
| 6 | 5 | 1 | 5 | 5 | 5 | 5 |
| | 1.25 | 1 | 4 | 5 | 5 | 5 |
| A | 5 | 2 | 3 | 1 | 5 | 5 |
| | 1.25 | 1 | 1 | 0 | 3 | 5 |
| B | 5 | 1 | 2 | 1 | 3 | 5 |
| | 1.25 | 0 | 0 | 0 | 2 | 5 |

TEST EXAMPLE 3

Seeds of corn and broad-leaved weeds such as cocklebur, common purslane and tall morningglory were sowed in the field as previously laid up in ridges, each ridge having an upper width of 1 m. At the time when the corn grew up to the 6-leaf stage and the broadleaved weeds up to 2 to 5-leaf stages, a designed amount of the test compound formulated into an emulsifiable concentrate according to Preparation Example 2 and dispersed in water was sprayed to the foliage of the test plants with three replications over the top by means of a small hand sprayer at a spray volume of 5 liters per are. After cultivation for 3 weeks, herbicidal activity and phytotoxicity were examined. The results are shown in Table 6.

TABLE 6

| Compound No. | Dosage (weight of active ingredient, g/are) | Phytotoxicity Corn | Herbicidal activity | | |
|---|---|---|---|---|---|
| | | | Cocklebur | Common purslane | Tall morningglory |
| 3 | 0.63 | 2 | 5 | 5 | 5 |
| | 0.32 | 1 | 5 | 5 | 4 |
| | 0.16 | 1 | 5 | 5 | 4 |
| A | 1.25 | 1 | 4 | 3 | 2 |
| | 0.63 | 0 | 1 | 2 | 2 |
| B | 1.25 | 1 | 4 | 4 | 4 |
| | 0.63 | 1 | 2 | 3 | 3 |

TEST EXAMPLE 4

Plastic trays (35 cm × 25 cm × 15 cm) were filled with upland field soil, and the seeds of tall morningglory, velvetleaf and sicklepod and the seeds of corn were sowed therein. A designed amount of the test compounds formulated into a wettable powder according to Preparation Example 1 was dispersed in water and applied by spraying at a spray volume of 5 liters per are to the whole surface of the soil. After the spraying, the test plants were placed in a greenhouse and grown for 20 days, and herbicidal activity and phytotoxicity were examined. The results are shown in Table 7.

TABLE 7

| Compound No. | Dosage (weight of active ingredient, g/are) | Phytotoxicity Corn | Herbicidal activity | | |
|---|---|---|---|---|---|
| | | | Tall morningglory | Sicklepod | Velvetleaf |
| 1 | 10 | 0 | 5 | 4 | 5 |
| | 5 | 0 | 4 | 4 | 5 |
| 2 | 10 | 1 | 5 | 4 | 5 |
| | 5 | 0 | 4 | 4 | 5 |
| 4 | 10 | 0 | 5 | 4 | 5 |
| | 5 | 0 | 4 | 4 | 5 |
| A | 10 | 3 | 0 | 1 | 4 |
| | 5 | 2 | 0 | 0 | 3 |
| B | 10 | 0 | 0 | 1 | 3 |
| | 5 | 0 | 0 | 0 | 1 |

TEST EXAMPLE 5

Plastic beakers (diameter 10 cm; height, 10 cm) were filled with upland field soil, and the seeds of corn, cotton and soybean and the seeds of morningglory, velvetleaf, Johnsongrass and green foxtail were separately sowed in the beakers. A designed amount of the test compound was sprayed over the top by means of a small hand sprayer. After the spraying, the test plants were grown for 20 days in the greenhouse, and herbicidal activity and phytotoxicity were examined. The results are shown in Table 8. In this pre-emergence treatment, the test compounds were formulated into an emulsifiable concentrate according to Preparation Example 2 and applied at a spray volume of 5 liters per are by dispersing it in water with the addition of a spreading agent.

TABLE 8

| Compound No. | Dosage (weight of active ingredient, g/are) | Phytotoxicity | | | Herbicidal activity | | | |
|---|---|---|---|---|---|---|---|---|
| | | Corn | Cotton | Soybean | Morning-glory | Velvetleaf | Johnsongrass | Green foxtail |
| 3 | 10 | 1 | 2 | — | 5 | 5 | 5 | 5 |
|   | 2.5 | 1 | 0 | — | 4 | 5 | 4 | 4 |
| 5 | 10 | 1 | 2 | 2 | 5 | 5 | 5 | 5 |
|   | 2.5 | 0 | 1 | 0 | 4 | 5 | 4 | 4 |
| 6 | 10 | 0 | — | — | 4 | 5 | 4 | 4 |
|   | 2.5 | 0 | — | — | — | 4 | 4 | 4 |
| A | 10 | 2 | — | — | 2 | 5 | 3 | 4 |
|   | 2.5 | 0 | — | — | 1 | 4 | 1 | 1 |
| B | 20 | 1 | — | — | 1 | 3 | 2 | 0 |
|   | 5 | 0 | — | — | 0 | 1 | 1 | 0 |

TEST EXAMPLE 6

Wagner's pots (1/5000 are) were filled with paddy field soil containing the seeds of broad-leaved weeds (e.g. monochoria, false pimpernel, toothcups) and the seeds of barnyardgrass and hardstem bulrush, and water was poured therein until the depth of water became 4 cm. Rice seedlings of the 3.5-leaf stage and the tubers of arrowhead were transplanted therein and grown for 2 days in a greenhouse. A designed amount of the test compound formulated in an emulsifiable concentrate according to Preparation Example 2 was applied to the pots by perfusion. Thereafter, the test plants were grown for an additional 3 weeks in the greenhouse, and herbicidal activity and phytotoxicity were examined. The results are shown in Table 9. In this treatment, the emusifiable concentrate was dispersed in water for application at a perfusion volume of 10 liters per are.

TABLE 9

| Compound No. | Dosage (weight of active ingredient, g/are) | Phytotoxicity Rice plant | Herbicidal activity | | | |
|---|---|---|---|---|---|---|
| | | | Barnyard-grass | Broad-leaved weed | Hardstem bulrush | Arrow-head |
| 3 | 2.5 | 1 | 5 | 5 | 5 | 5 |
|   | 1.25 | 1 | 5 | 5 | 4 | 4 |
| 5 | 2.5 | 1 | 5 | 5 | 5 | 5 |
|   | 1.25 | 1 | 5 | 5 | 4 | — |
| A | 2.5 | 1 | 2 | 5 | 3 | 0 |
|   | 1.25 | 0 | 1 | 5 | 2 | 0 |
| B | 2.5 | 0 | 3 | 5 | 2 | 0 |
|   | 1.25 | 0 | 1 | 5 | 1 | 0 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:
1. A compound of the formula:

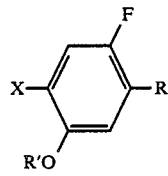

wherein X is a chlorine atom or a bromine atom, R is $NO_2$ or $NH_2$, and R' is a $C_3-C_4$ alkenyl group or a $C_3-C_4$ alkynyl group.

2. A compound according to claim 1 of the formula:

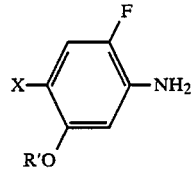

wherein X is a chlorine atom or a bromine atom and R' is a $C_3-C_4$ alkenyl group or a $C_3-C_4$ alkynyl group.

3. A compound according to claim 1 of the formula:

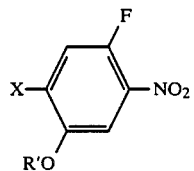

wherein X is a chlorine atom or a bromine atom and R' is a $C_3-C_4$ alkenyl group or a $C_3-C_4$ alkynyl group.

4. A compound according to claim 1, wherein X is chlorine.

5. A compound according to claim 1, wherein X is bromine.